US008707486B2

(12) United States Patent
Chella et al.

(10) Patent No.: US 8,707,486 B2
(45) Date of Patent: Apr. 29, 2014

(54) LACING SYSTEM TO SECURE A LIMB IN A SURGICAL SUPPORT APPARATUS

(75) Inventors: David E. Chella, Brighton, MA (US); Paul J. Skavicus, Maynard, MA (US)

(73) Assignee: Allen Medical Systems, Inc., Batesville, IN (US)

(*) Notice: Subject to any disclaimer, the term of this patent is extended or adjusted under 35 U.S.C. 154(b) by 462 days.

(21) Appl. No.: 13/027,413

(22) Filed: Feb. 15, 2011

(65) Prior Publication Data

US 2011/0197362 A1   Aug. 18, 2011

Related U.S. Application Data

(60) Provisional application No. 61/304,903, filed on Feb. 16, 2010.

(51) Int. Cl.
*A61G 13/10* (2006.01)
*A43C 11/14* (2006.01)
*A43C 11/20* (2006.01)

(52) U.S. Cl.
USPC ............. 5/650; 5/648; 5/624; 36/50.1; 36/64

(58) Field of Classification Search
USPC ................ 5/648–651, 624; 128/845; 602/32; 606/90; 24/68 SK; 36/64, 65, 50.1, 36/50.5, 117.1, 117.7–118.1
See application file for complete search history.

(56) References Cited

U.S. PATENT DOCUMENTS

| | | | | |
|---|---|---|---|---|
| 4,539,763 | A | * | 9/1985 | Walkhoff ................... 36/118.1 |
| 4,551,932 | A | * | 11/1985 | Schoch ....................... 36/117.1 |
| 4,573,482 | A | | 3/1986 | Williams, Jr. |
| 4,620,698 | A | | 11/1986 | Reed et al. |
| 4,886,258 | A | | 12/1989 | Scott |
| 5,052,128 | A | | 10/1991 | Lonardo |
| 5,177,882 | A | * | 1/1993 | Berger ........................... 36/50.1 |
| 5,249,377 | A | * | 10/1993 | Walkhoff ..................... 36/117.7 |
| 6,234,173 | B1 | | 5/2001 | Hajianpour |
| 6,289,558 | B1 | | 9/2001 | Hammerslag |
| 7,591,050 | B2 | | 9/2009 | Hammerslag |
| 2003/0056793 | A1 | | 3/2003 | Atwater et al. |
| 2011/0197362 | A1 | * | 8/2011 | Chella et al. ..................... 5/650 |

OTHER PUBLICATIONS

European search report from EP 11 15 4689 dated Jul. 6, 2011, 5 pages.

* cited by examiner

*Primary Examiner* — Robert G Santos
(74) *Attorney, Agent, or Firm* — Barnes & Thornburg LLP (57) ABSTRACT

A surgical support apparatus comprising a surgical boot sized to receive a portion of a limb of a patient therein and a tightening device positioned between a first end and a second end of the surgical boot. The tightening device is configured to apply a clamping force to the portion of the limb of the patient positioned in the surgical boot.

11 Claims, 12 Drawing Sheets

LACING SYSTEM TO SECURE A LIMB IN A SURGICAL SUPPORT APPARATUS

CROSS-REFERENCE TO RELATED APPLICATIONS

The present application claims the benefit, under 35 U.S.C. §119(e), of U.S. Provisional Application No. 61/304,903 which was filed Feb. 16, 2010 and which is hereby incorporated by reference herein.

BACKGROUND

The present disclosure relates to a system for securing a limb in a surgical support apparatus. More particularly, the present disclosure relates to an arm sheath, a surgical boot, or other limb holding device including one or more tightening devices for restraining a portion of a patient's limb.

SUMMARY

The present invention comprises an apparatus and/or method that has any one or more of the features listed in the appended claims and/or any one or more of the following features, which alone or in any combination may comprise patentable subject matter:

According to one aspect, a surgical support apparatus includes a surgical boot sized to receive a portion of a limb of a patient therein that has a shell and a tongue, and a tightening device positioned between a first end and a second end of the surgical boot. The tightening device is configured to draw the tongue toward the shell such that a clamping force is applied to the portion of the limb of the patient positioned in the surgical boot.

In some embodiments, the tightening device may be a rotary lacing system. Additionally, in some embodiments, the rotary lacing system may include a rotary tightening mechanism, a cable coupled at each end to the rotary tightening mechanism, and a pair of guides sized to receive the cable. In some embodiments, the rotary tightening mechanism may be coupled to the tongue of the surgical boot.

In some embodiments, each of the guides may be coupled to shell of the surgical boot. In some embodiments, the rotary tightening mechanism may include a reel body coupled to the tongue that receives each end of the cable, a knob rotatively coupled to the reel body such that rotating the knob in a first direction may draw each end of the cable into the reel body and draw the tongue toward the shell to thereby increase the tension of the cable. Additionally, in some embodiments, one of the guides may include a cradle coupled to the shell, and a handle removably coupled to the cradle. The handle may have a channel defined therein sized to receive the cable.

In some embodiments, the surgical boot may include a second tightening device positioned between the first tightening device and the first end of the surgical boot. In some embodiments, the second tightening device may be a strap mechanism. In some embodiments, the strap mechanism may include a ladder strap having a number of teeth and a buckle sized to receive the ladder strap.

According to another aspect, the surgical support apparatus includes an arm sheath sized to receive a portion of a limb of a patient therein. The surgical support apparatus also includes a tightening device coupled to the arm sheath between a first end and a second end of the arm sheath. The tightening device is configured to apply a clamping force to the portion of the limb of the patient positioned in the arm sheath.

In some embodiments, the tightening device may be a rotary lacing system that includes a rotary tightening mechanism, a cable coupled at each end to the rotary tightening mechanism, and a pair of guides formed in the arm sheath that receive the cable. In some embodiments, the surgical support apparatus may include a load apparatus coupled to an end of the arm sheath, and the load apparatus may be configured to place the limb of the patient in tension.

According to another aspect, the surgical support apparatus includes a limb holding device sized to receive a portion of a limb of a patient therein, a first clamping means for applying a first clamping force to the portion of the limb of the patient received in the limb holding device, and a second clamping means for applying a second clamping force to the portion of the limb of the patient received in the limb holding device. The portion of the limb of the patient is held substantially immobile by the first clamping means and the second clamping means.

According to another aspect, the surgical support apparatus includes a surgical boot sized to receive a portion of a limb of a patient therein that includes a shell and a tongue, a rotary lacing system positioned between a first end and a second end of the surgical boot, and a strap mechanism positioned between the rotary lacing system and the first end of the surgical boot. The rotary lacing system and strap mechanism are configured to draw the tongue toward the shell such that a clamping force is applied to the portion of the limb of the patient positioned in the surgical boot.

Additional features will become apparent to those skilled in the art upon consideration of the following detailed description of illustrative embodiments exemplifying the best mode as presently perceived.

BRIEF DESCRIPTION OF THE DRAWINGS

The detailed description particularly refers to the accompanying figures in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the surgical support apparatus described herein and a patient's natural anatomy. Such terms have well-understood meanings in both the study of anatomy and the surgical field. Use of such anatomical reference terms in the specification and claims is intended to be consistent with their well-understood meanings unless noted otherwise.

Figure 1:
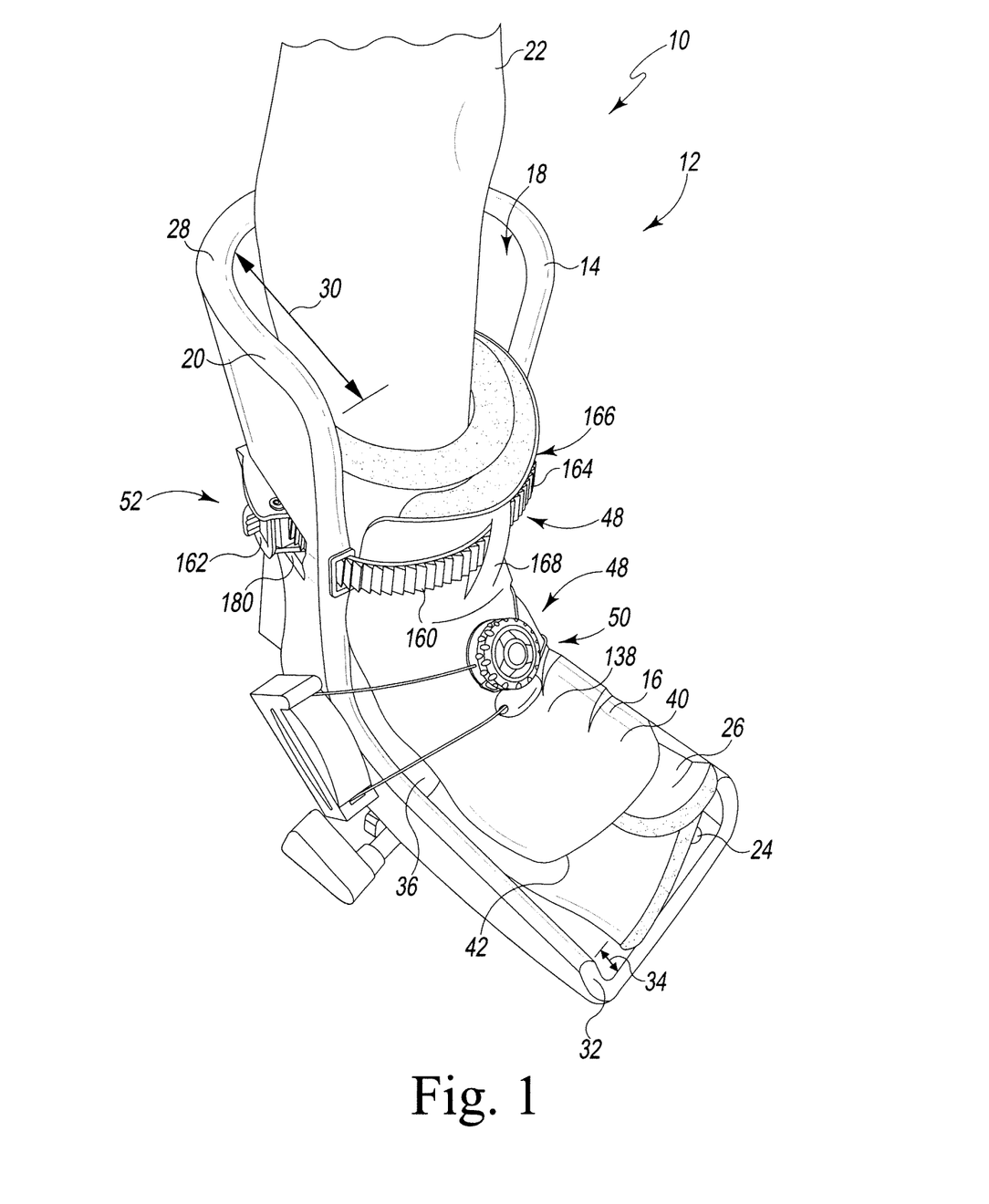
FIG. 1 is a perspective view of one embodiment of a surgical support apparatus is shown with a rotary lacing system.

Referring to FIG. 1, a surgical support apparatus 10 is shown embodied as a surgical boot 12, which is used to support a lower portion of a patient's foot and leg during a surgical procedure. It will be appreciated that the surgical support apparatus 10 may be alternatively embodied as an arm sheath that supports a portion of a patient's arm or hand, a neck brace that rigidly supports a patient's neck and head, or any other support device configured to support a portion of a patient's body.

Figure 7:
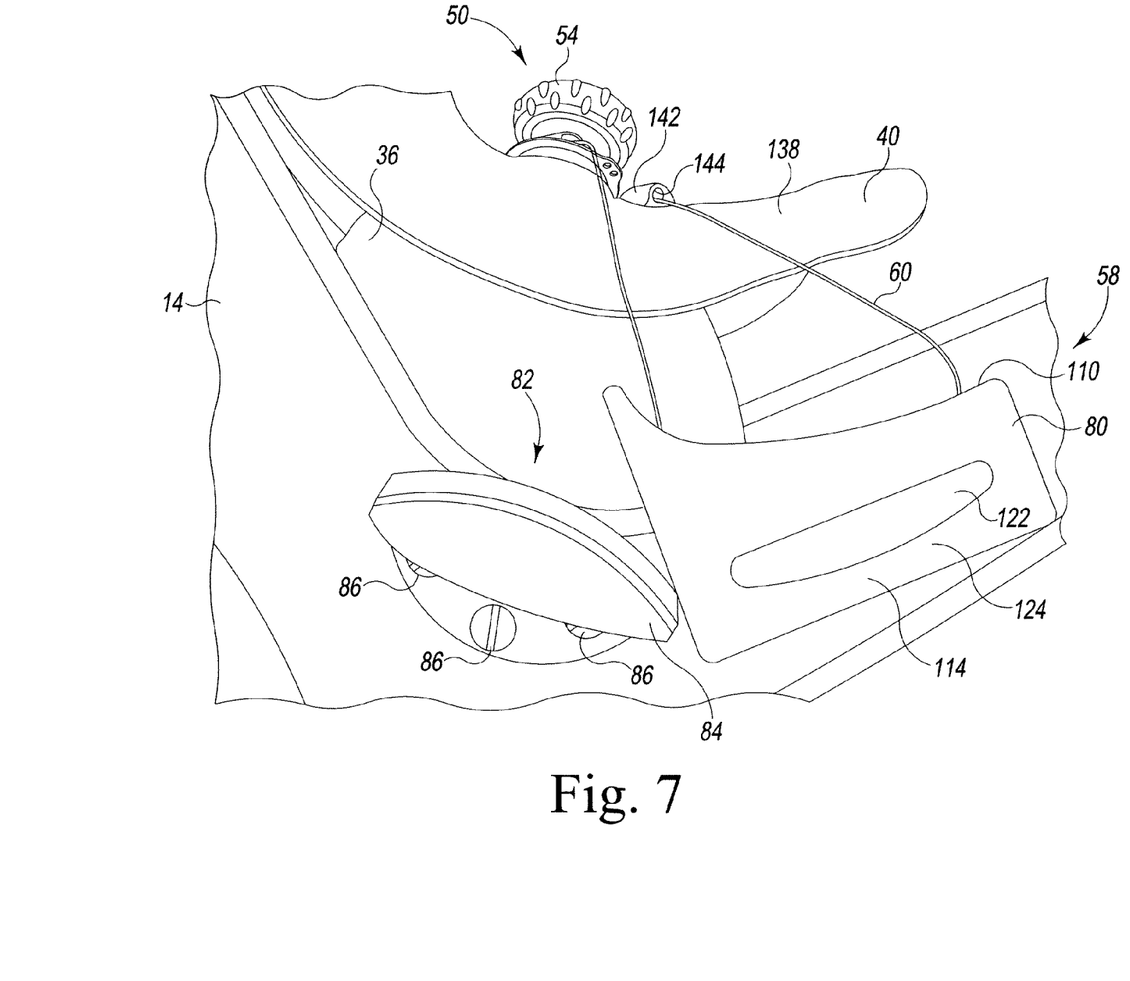
FIG. 7 is another fragmentary side elevation view of the surgical support apparatus of FIG. 1 showing the guide removed from the cradle.
Figure 8:
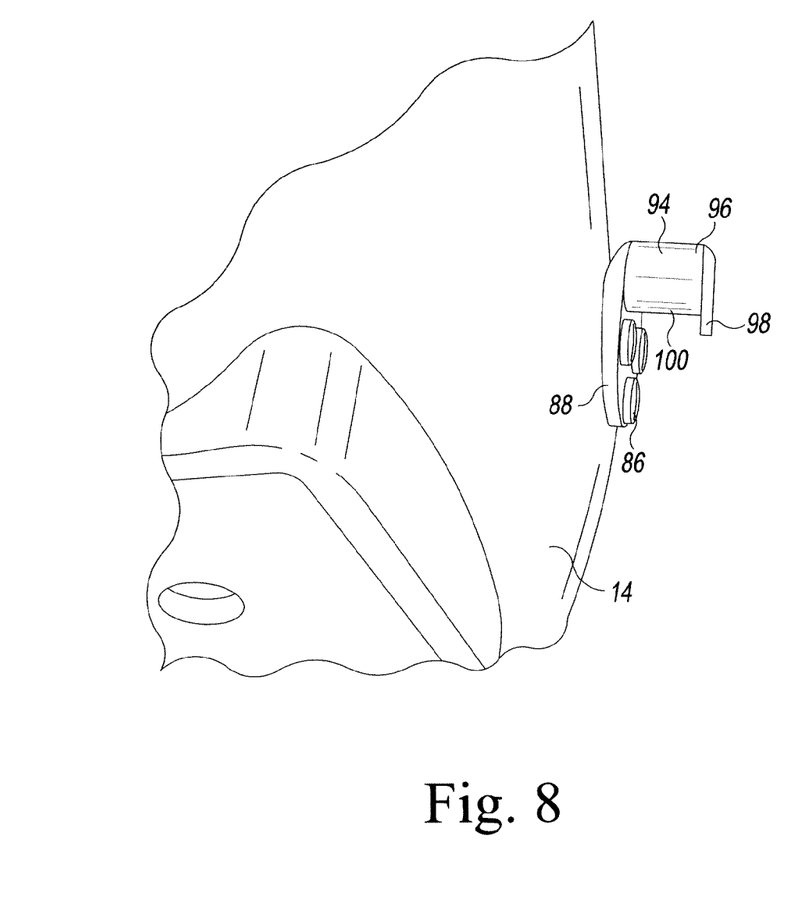
FIG. 8 is a fragmentary rear perspective view of the surgical support apparatus of FIG. 1 showing the cradle in profile.
Figure 9:
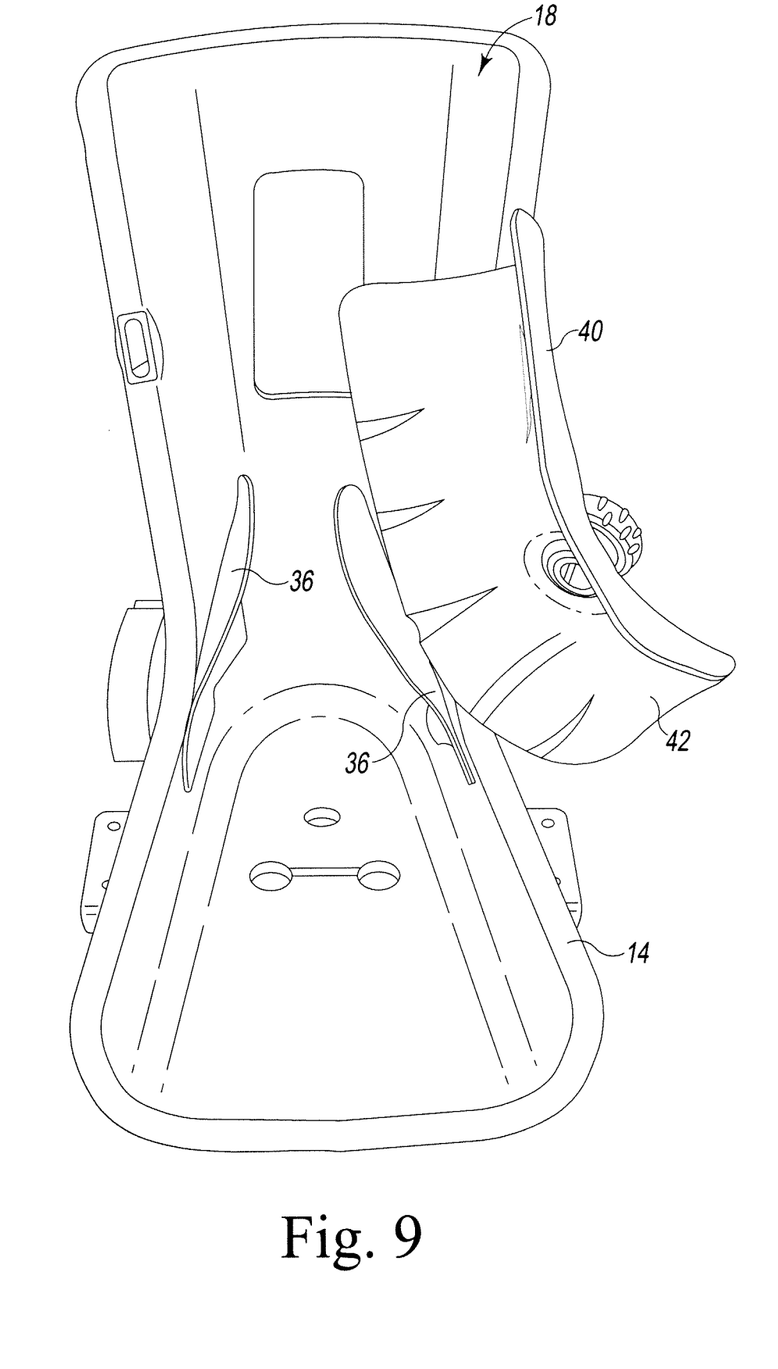
FIG. 9 is another perspective view of the surgical support apparatus of FIG. 1 showing the rotary lacing system and the tongue unlatched.

Referring now to FIGS. 1-9, the surgical boot 12 includes a shell 14 and a tongue 16. The shell 14 is formed from rigid or semi-rigid plastic material and has a generally L-shape. The shell 14 has a channel 18 defined by a rim 20 that is sized to receive a lower portion of a leg 22 and a foot 24, which are wrapped in a foam pad 26. At an upper end 28 of the shell 14, the channel 18 extends a depth 30; at a lower end 32, the channel 18 has a depth 34. As embodied in FIGS. 1-9, the depth 30 is greater than the depth 34. As best seen in FIG. 9, the shell 14 also includes a pair of rigid or semi-rigid plastic flaps 36 that are secured to the channel 18.

The tongue 16 includes a curved body 40 formed from a rigid or semi-rigid plastic material. As shown in FIGS. 1-9, the tongue 16 and the shell 14 are formed as separate components. It should also be appreciated that in other embodiments the shell 14 and the tongue 16 may be made integral. The curved body 40 is shaped to fit over the anterior side of the leg 22 and the foot 24. When the leg 22 and the foot 24 are positioned in the surgical boot 12, the curved body 40 is positioned opposite the heel (not shown) of the foot 24 received in the channel 18 of the shell 14. An inner surface 42 of the curved body 40 contacts the pair of rigid or semi-rigid plastic flaps 36 of the shell 14. In that way, the shell 14 and the tongue 16 enclose the lower portion of the leg 22 and the foot 24 therebetween. As will be described in greater detail below, the shell 14 and the tongue 16 cooperate to rigidly hold the lower portion of the leg 22 and the foot 24 within the surgical boot 12. It should also be appreciated that in other embodiments the surgical boot 12 may include a pair of flaps rather than a tongue. In such embodiments, the shell 14 and the pair of flaps would cooperate to hold the lower portion of the leg 22 and the foot 24 within the surgical boot 12.

The surgical boot 12 also includes a pair of tightening devices 48 configured to draw the tongue 16 toward the shell 14 such that a clamping force is applied to the lower portion of the leg 22 and the foot 24. The tightening device 48 positioned between the upper end 28 and the lower end 32 of the shell 14 is a rotary lacing system 50, while the tightening device 48 positioned between the rotary lacing system 50 and the upper end 28 of the shell 14 is a strap mechanism 52. It will be appreciated that in other embodiments the surgical boot 12 may include additional and/or alternative tightening devices 48.

Figure 2:
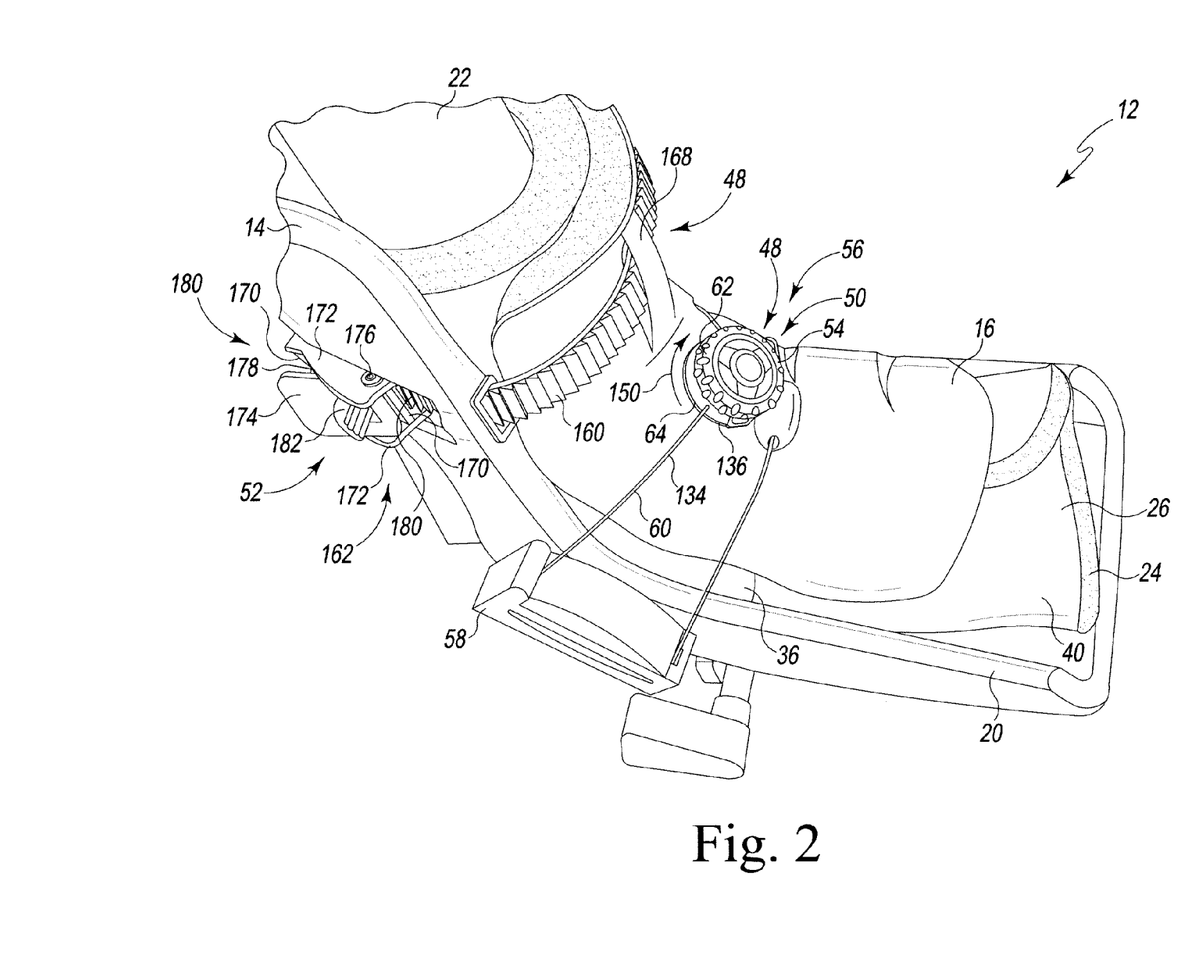
FIG. 2 is another perspective view of the surgical support apparatus of FIG. 1.
Figure 3:
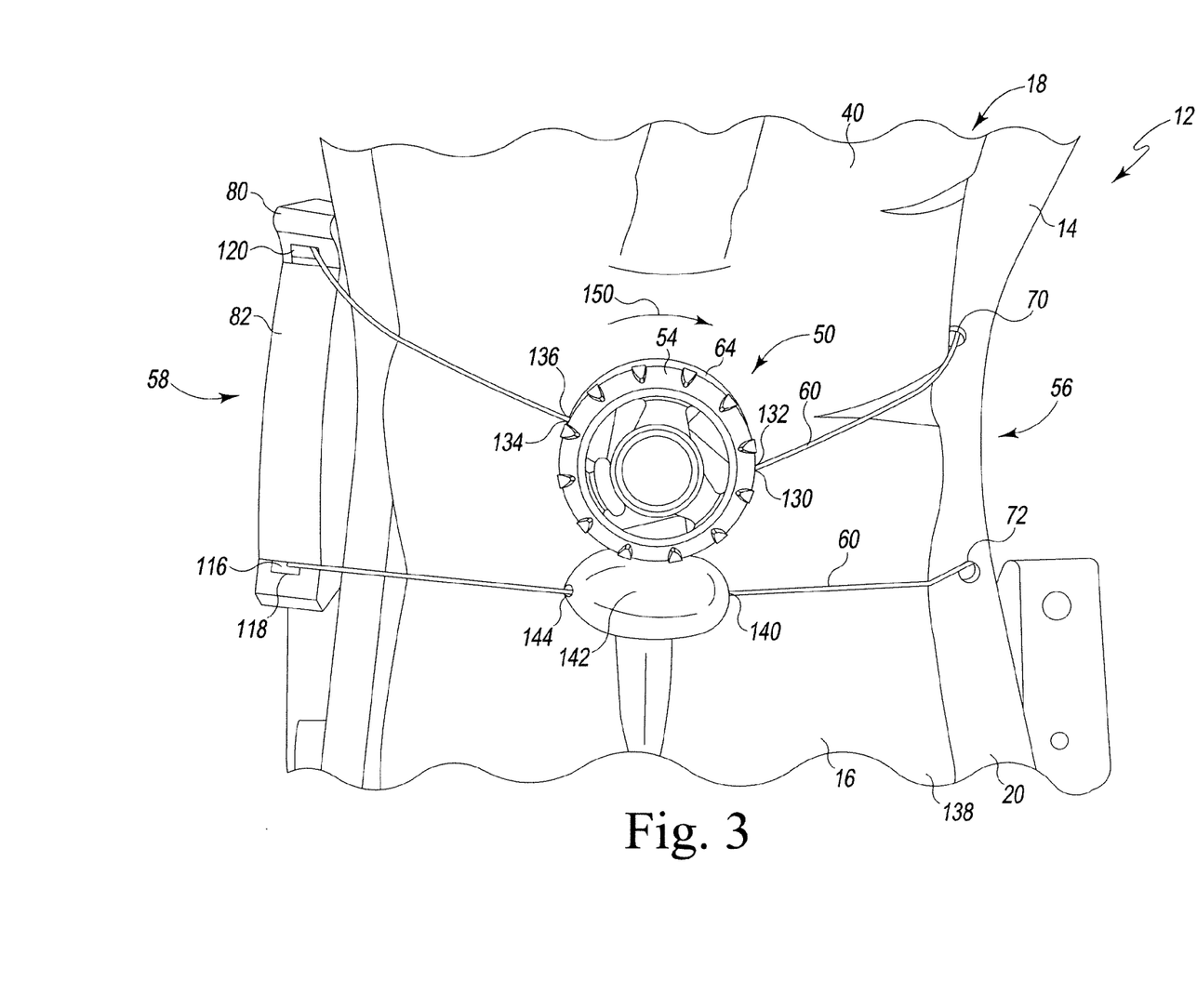
FIG. 3 is a fragmentary front elevation view of the surgical support apparatus of FIG. 1.
Figure 4:
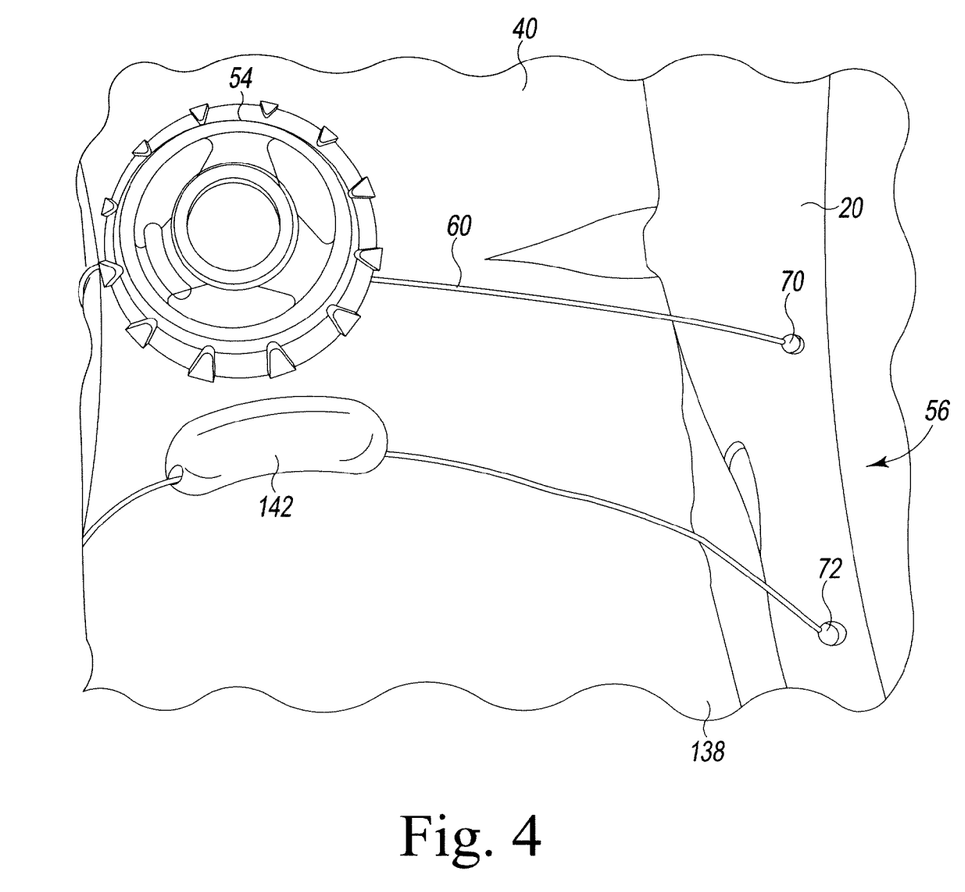
FIG. 4 is another fragmentary front elevation view of the surgical support apparatus of FIG. 1.
Figure 5:
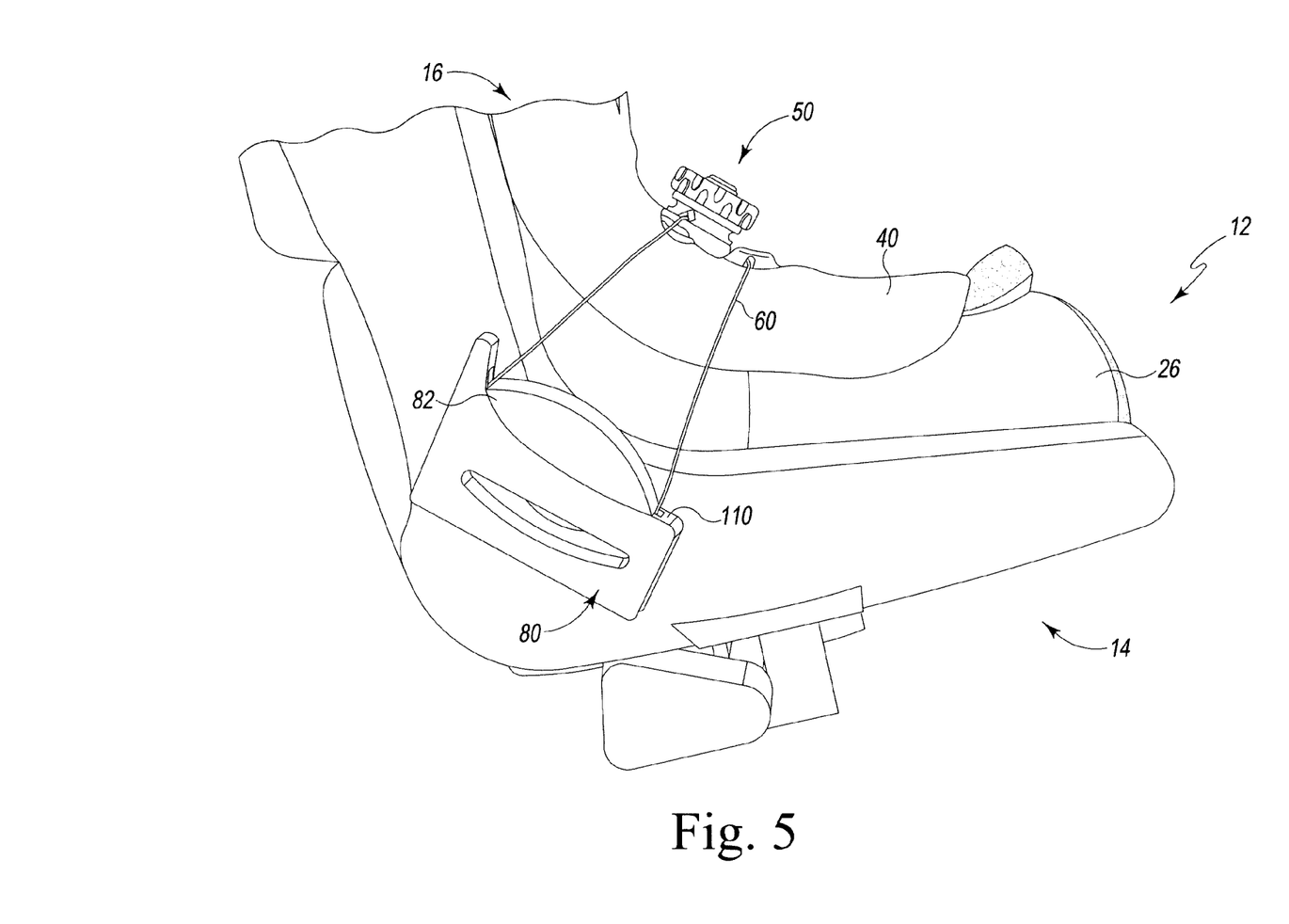
FIG. 5 is a fragmentary side elevation view of the surgical support apparatus of FIG. 1.

As shown in FIGS. 2-3, the rotary lacing system 50 includes a rotary tightening mechanism 54, guides 56, 58, and a cable 60 coupled to the rotary tightening mechanism 54 and routed through the guides 56, 58. The rotary tightening mechanism 54 includes a knob 62 and a reel body 64 coupled to the curved body 40 of the tongue 16. It will be appreciated that in other embodiments the rotary tightening mechanism 54 may not be coupled to the tongue 16. One example of a rotary tightening mechanism 54 is a Boa High Power Reel—Series 40 Coiler, commercially available from Boa Technology, Inc. of Steamboat Springs, Colo., U.S.A. U.S. Pat. No. 6,289,558, which is entitled "Footwear Lacing System," describes an exemplary rotary tightening mechanism 54 and is expressly incorporated herein by reference. U.S. Pat. No. 7,591,050, which is also entitled "Footwear Lacing System," describes an exemplary embodiment of rotary tightening mechanism 54 and is expressly incorporated herein by reference.

As shown in FIG. 3, the guides 56, 58 are positioned on either side of the channel 18 of the shell 14. The guide 56 includes a pair of holes 70, 72 that are formed in the rim 20 of the shell 14. The cable 60 is received through the hole 70 of the rim 20 into the interior (not shown) of the shell 14 and is guided along the back surface (not shown) of the rim 20 to the hole 72. In some embodiments, the guide 56 may include a track positioned within the interior of the shell 14 between the holes 70, 72. In some embodiments, the track may be formed from hardened plastic or metallic material that resists wear. The cable 60 passes out of the interior of the shell 14 through the hole 72 of the rim 20. It will be appreciated that in other embodiments the guide 56 may be a separate structure coupled to the shell 14.

The guide 58 is positioned on the opposite side of the channel 18 of the shell 14. As shown in FIGS. 5-8, the guide 58 includes a handle 80 that may be detached from a cradle 82 such that the surgical boot 12 may be removed from the lower portion of the leg 22 and the foot 24. As best seen in FIGS. 7 and 8, the cradle 82 is a metal bracket 84 that is secured to the shell 14 by a number of fasteners 86. It will be appreciated that in other embodiments the bracket 84 may be formed from rigid or hardened plastic materials. It will be appreciated that in other embodiments the guide 68 may be formed in the rim 20 and take a form similar to that of the guide 56.

The bracket 84 of the guide 58 has a plate 88 that is positioned adjacent to the shell 14. Each of the fasteners 86 extends through an opening (not shown) formed in the plate 88 and is received in a corresponding hole (not shown) formed in the shell 14. As best seen in FIG. 8, a mounting arm 94 extends outwardly from the plate 88 to an end 96. A flange 98 extends downwardly from the end 96 such that a channel 100 is defined between the flange 98 and the plate 88.

Figure 6:
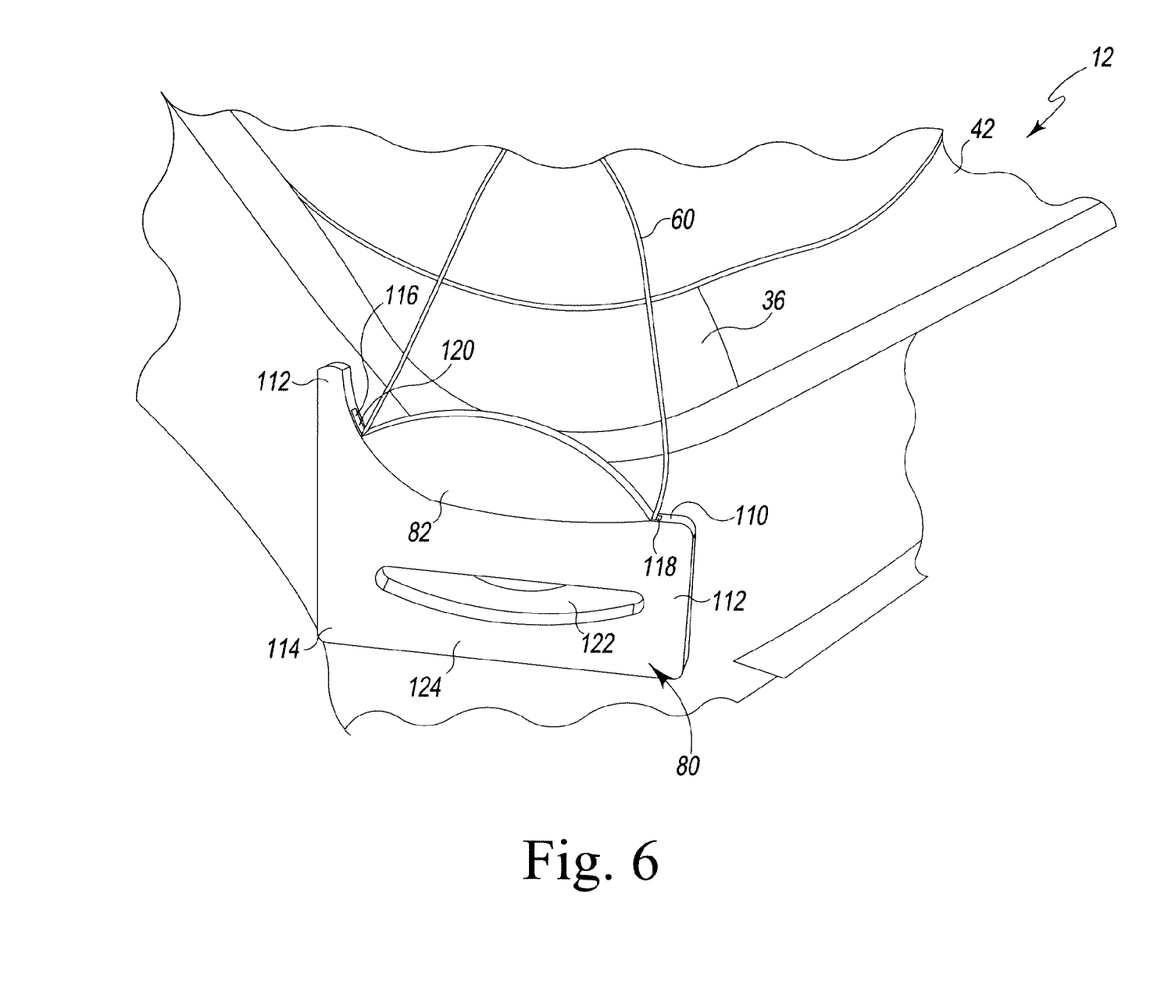
FIG. 6 is another fragmentary side elevation view of the surgical support apparatus of FIG. 1.

As shown in FIG. 6, the channel 100 is sized to receive an upper end 110 of the handle 80. The handle 80 includes a body 112 extending from the upper end 110 to a lower end 114. A track 116 is formed in the body 112 at the upper end 110 and is sized to receive and retain the cable 60 therein. The cable 60 is received in one end 118 of the track 116 and is guided along the length of track 116 to another end 120.

The body 112 of the handle 80 also includes an opening 122 that extends through the body 112 between the upper end 110 and the lower end 114. A grip 124 is formed at the lower end 114, and the grip 124 and the opening 122 are sized to receive a hand of a user. To detach the handle 80 from the cradle 82, the user grasps the grip 124 and pulls downward, away from the mounting arm 94. Once the upper end 110 of the handle 80 is removed from the channel 100, the user then pulls the handle 80 outward, away from the shell 14, such that handle 80 is free of the cradle 82. As shown in FIGS. 7 and 9, when the handle 80 is free of the cradle 82, the surgical boot 12 may be removed from the lower portion of the leg 22 and the foot 24.

Returning to FIG. 3, the path of the cable 60 is shown. The cable 60 is a braided metal wire extending from an end 130 received in a mount 132 of the reel body 64 to an end 134 received in a mount 136 of the reel body 64. Extending from the end 130, the cable 60 is routed to the guide 56 and through the hole 70. The cable 60 is then guided along the interior of shell 14 and out the hole 72. As described above, the cable 60 then extends along the outer surface 138 of the curved body 40 and is received in an opening 140 of another guide 142. As shown in the embodiment of FIGS. 1-9, the wire guide 142 is formed in the semi-rigid or rigid plastic of the curved body 40 of the tongue 16. In other embodiments the guide 142 may be formed from cloth, metal, or other material. In other embodiments, the guide 142 may also be manufactured as a separate piece and coupled the curved body 40 during assembly of the surgical boot 12.

The cable 60 exits the guide 142 through an opening 144 and extends along the outer surface 138 of the curved body 40 before being received in the end 118 of the track 116 of the handle 80. As described above, the cable 60 is guided along the length of track 116 before exiting through the end 120. The cable 60 is then routed to the tightening mechanism 54 and the end 134 is received in the mount 136 of the reel body 64. It should also be appreciated that in other embodiments the cable 60 may follow a different path through the shell 14 and the tongue 16.

When the knob 62 of the tightening mechanism 54 is rotated in the direction indicated by arrow 150 in FIGS. 2 and 3, the ends 130, 134 of the cable 60 are drawn into the reel body 64, thereby reducing slack and increasing tension in cable 60. As slack in the cable 60 is reduced, the tongue 16 is drawn toward the shell 14. The movement of the tongue 16 toward the shell 14 applies a clamping force to the lower portion of the leg 22 and the foot 24. When sufficient clamping force is applied, the shell 14 and the tongue 16 cooperate to rigidly hold the lower portion of the leg 22 and the foot 24 within the surgical boot 12. A release lever (not shown) is used to release tension in the cable 60 and allow the surgical boot 12 to be removed from the lower portion of the leg 22 and the foot 24.

Returning to FIGS. 1 and 2, the strap mechanism 52 is positioned between the rotary lacing system 50 and the upper end 28 of the shell 14 and is also configured to draw the tongue 16 toward the shell 14 such that a clamping force is applied to the lower portion of the leg 22 and the foot 24. The strap mechanism 52 includes a ladder strap 160 and a buckle 162. The strap 160 includes a number of teeth 164 positioned along the length of strap 160. The strap 160 has an end 166 that is secured to the shell 14 on the opposite side of the channel 18 from the buckle 162. The strap 160 extends from the end 166 over the outer surface 138 of the curved body 40 and is received in a guideway 168. As shown in FIG. 2, the guideway 168 is formed in the semi-rigid or rigid plastic of the curved body 40. In other embodiments the guideway 168 may be formed from cloth, metal, or other material. In other embodiments, the guideway 168 may also be manufactured as a separate piece and coupled the curved body 40 during assembly of the surgical boot 12.

After passing through the guideway 168, the strap 160 extends over the outer surface 138 of the curved body 40 and is received in the buckle 162. The buckle 162 includes a mounting plate 170 coupled to the shell 14. The mounting plate 170 includes a pair of arms 172 that extend outwardly from the mounting plate 170. A body 174 is rotatably coupled to the arms 172 via a pair of pivot joints 176. A slot 180 is defined between the plate 170 and the body 174. When the body 174 is placed in an open position (see FIG. 2), the strap 160 is permitted to move freely within the slot 180. When the body 174 is placed in a closed position, a clasp 178 secured to the body 174 engages with the teeth 164 of the strap 160 and prevents the strap 160 from moving. The body 174 also includes a release lever 182 that releases the clasp 178 and allows the user to move the strap 160.

To tighten the strap mechanism 52, the body 174 is placed in the open position and the strap 160 is moved through the slot 180 until the lower portion of the leg 22 and the foot 24 are positioned snugly between the channel 18 of the shell 14 and the curved body 40 of the tongue 16. The body 174 is then placed in the closed position. As the body 174 is moved from the open position to the closed position, the clasp 178 engages with the teeth 164 of the strap 160 and draws an additional length of the strap 160 through the slot 180, thereby drawing the tongue 16 toward the shell 14 and applying a clamping force to the lower portion of the leg 22 and the foot 24. When sufficient clamping force is applied, the shell 14 and the tongue 16 cooperate to rigidly hold the lower portion of the leg 22 and the foot 24 within the surgical boot 12.

It will be appreciated that in other embodiments the strap mechanism 52 may be replaced by another rotary tightening mechanism similar to rotary tightening mechanism 54. It will also be appreciated that in other embodiments the surgical boot 12 may include additional rotary tightening mechanisms 54 to apply additional clamping forces to the lower portion of the leg 22 and the foot 24.

Figure 10:
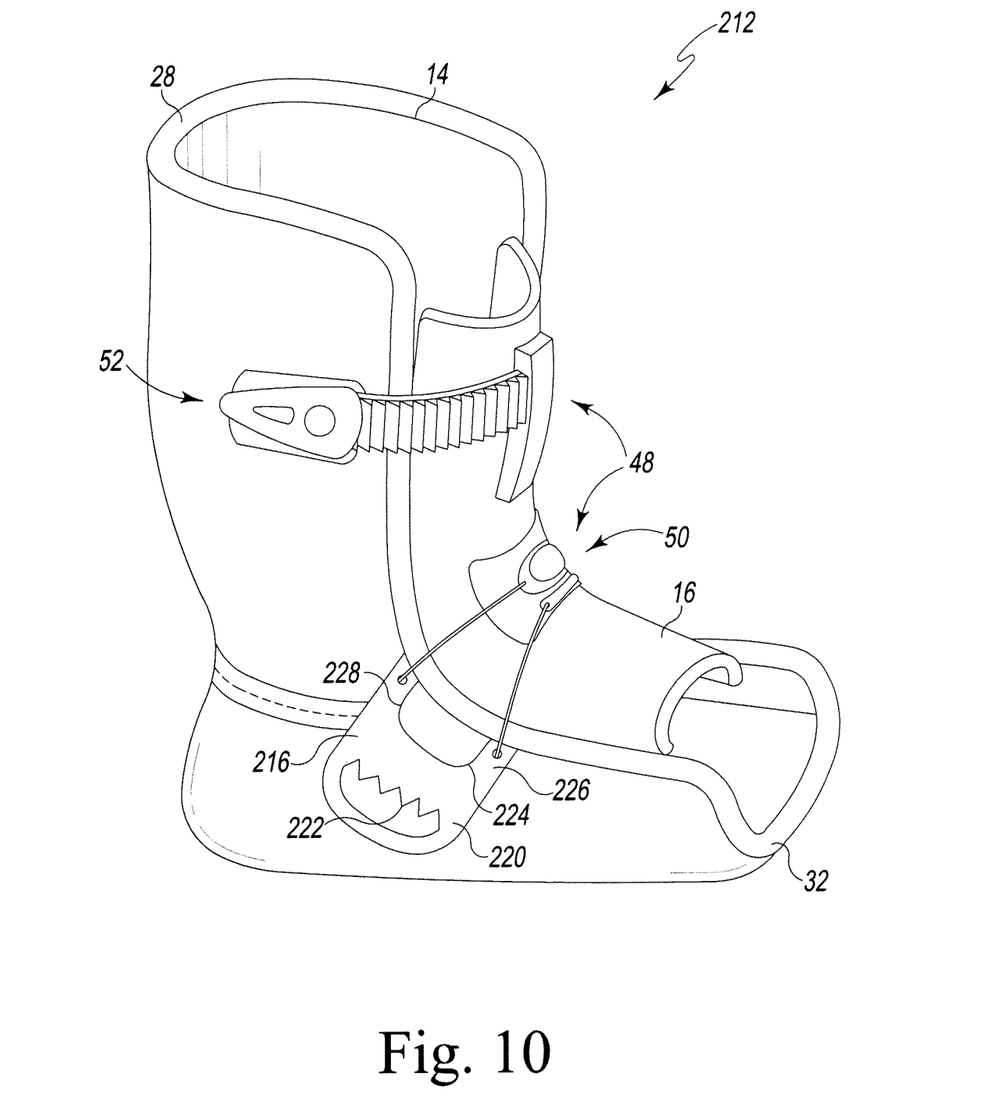
FIG. 10 is a perspective view of another embodiment of a surgical support apparatus with a rotary lacing system.

Referring now to FIG. 10, another embodiment of a surgical boot 12 is shown (hereinafter referred to as surgical boot 212). Some features of the embodiment illustrated in FIG. 10 are substantially similar to those discussed above in reference to the embodiment of FIGS. 1-9. Such features are designated in FIG. 10 with the same reference numbers as those used in FIGS. 1-9. Surgical boot 212 includes a shell 14, a tongue 16, and a pair of tightening devices 48 configured to draw the tongue 16 toward the shell 14 such that a clamping force is applied to a lower portion of a leg and a foot. The tightening device 48 positioned between an upper end 28 and a lower end 32 of the shell 14 is a rotary lacing system 50, while the tightening device 48 positioned between the rotary lacing system 50 and the upper end 28 of the shell 14 is a strap mechanism 52.

The handle 220 includes a contoured grip 222 sized to receive a hand of user. The handle 220 also include a slot 224 formed on an upper end 226 sized to receive a cradle 228. Similar to the cradle 82 of the embodiment of FIGS. 1-9, the cradle 228 is coupled to the shell 14.

Figure 11:
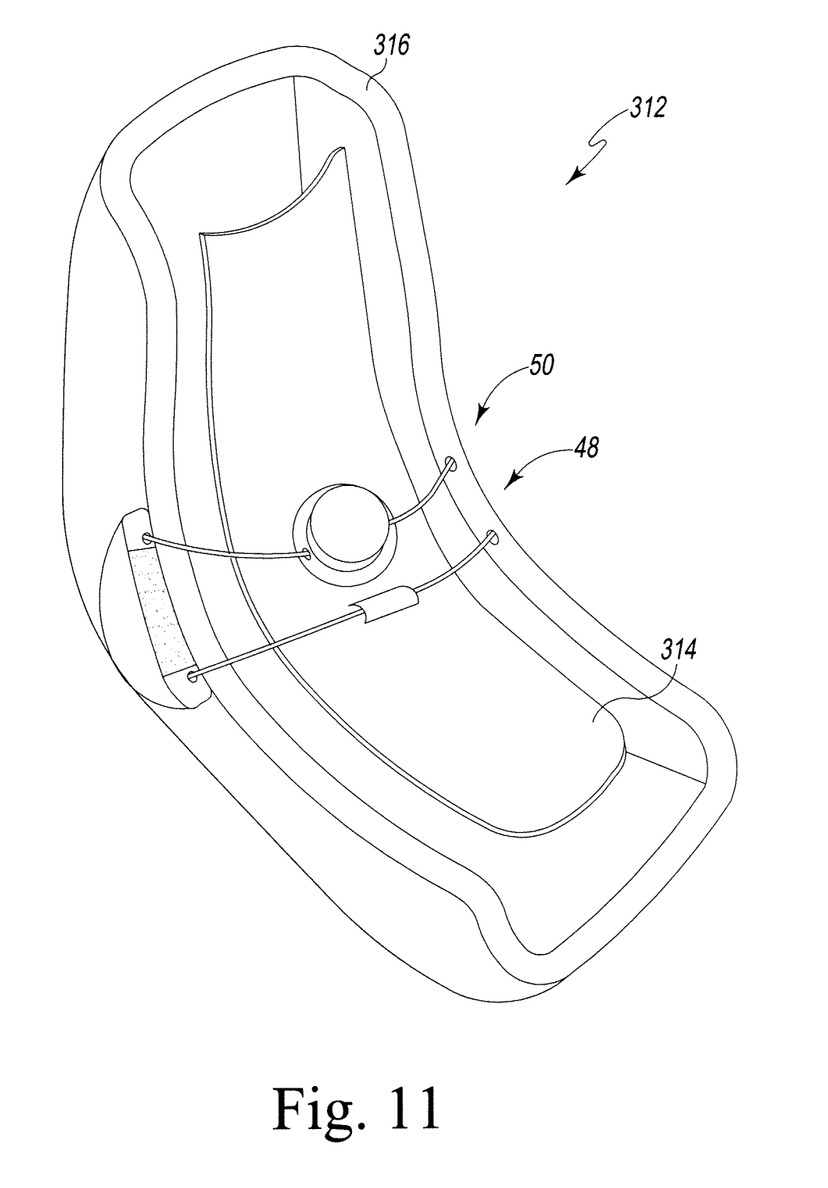
FIG. 11 is a perspective view of another embodiment of a surgical support apparatus with a rotary lacing system.

Referring now to FIG. 11, another embodiment of a surgical boot 12 is shown (hereinafter referred to as surgical boot 312). Some features of the embodiment illustrated in FIG. 11 are substantially similar to those discussed above in reference to the embodiment of FIGS. 1-9. Such features are designated in FIG. 11 with the same reference numbers as those used in FIGS. 1-9. Surgical boot 312 includes another shell 314 and tongue 316. The surgical boot 312 includes only a single tightening device 48, embodied as a rotary lacing system 50, configured to draw the tongue 316 toward the shell 314 such that a clamping force is applied to a lower portion of a leg and a foot.

Figures 12, 12A:
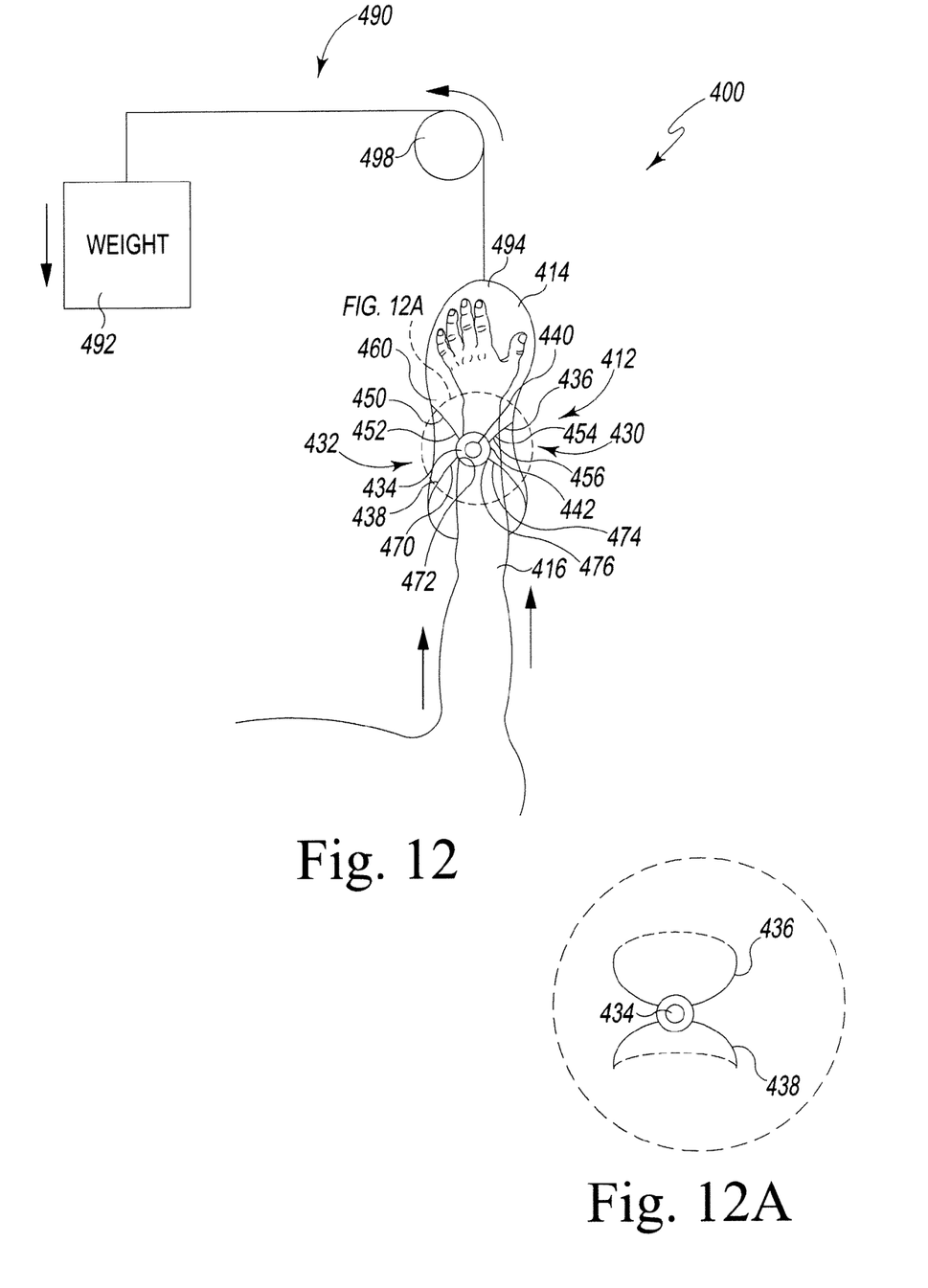
FIG. 12 is a diagrammatic view of another embodiment of a surgical support apparatus with a rotary lacing system.
FIG. 12A is a diagrammatic view showing the rotary lacing system and cable of the surgical support apparatus of FIG. 12.

Referring now to FIGS. 12 and 12A, a surgical support apparatus 400 is shown embodied as an arm sheath 412, which is used to support a portion of a patient's arm during a surgical procedure. The arm sheath 412 includes a plate 414 sized to receive a portion of an arm 416. In some embodiments, the portion of the arm 416 may be wrapped in a foam pad or other protective material.

The arm sheath 412 also includes a tightening device 430 configured to apply a clamping force to the portion of the arm 416. It will be appreciated that in other embodiments the arm sheath 412 may include additional and/or alternative tightening devices 430. As shown in FIG. 12, the tightening device 430 is a rotary lacing system 432 including a rotary tightening mechanism 434 and a pair of cables 436, 438 coupled to the rotary tightening mechanism 434. The rotary tightening mechanism 434 includes a knob 440 and a reel body 442. One example of a rotary tightening mechanism 434 is a Boa High Power Reel—Series 40 Coiler, commercially available from Boa Technology, Inc. of Steamboat Springs, Colo., U.S.A. U.S. Pat. No. 6,289,558, which is entitled "Footwear Lacing System," describes an exemplary rotary tightening mechanism 54 and is expressly incorporated herein by reference. U.S. Pat. No. 7,591,050, which is also entitled "Footwear Lacing System," describes an exemplary embodiment of rotary tightening mechanism 54 and is expressly incorporated herein by reference.

Each of the cables 436, 438 is embodied as a braided metal wire. It will be appreciated that in other embodiments the cables may be formed from plastic or cloth material. The cable 436 extends from an end 450 received in a mount 452 of the reel body 442 to an end 454 received in another mount 456 of the reel body 442. Extending from the end 450, the cable 436 is routed under one side 460 of the plate 414 and along the back surface of the plate 414. In some embodiments, the plate 414 may include a number of guides sized to receive the cable 436 and route the cable 436 around the plate 414.

The cable 438 extends from an end 470 received in a mount 472 of the reel body 442 to an end 474 received in another mount 476 of the reel body 442. Extending from the end 470, the cable 438 is routed under one side 480 of the plate 414 and along the back surface of the plate 414. In some embodiments, the plate 414 may include a number of guides sized to receive the cable 438 and route the cable 438 around the plate 414.

When the knob 440 of the tightening mechanism 434 is rotated in a first direction, the ends 450, 454, 470, 474 of the cables 436, 438 are drawn into the reel body 442, thereby reducing slack and increasing tension in cables 436, 438. As slack in each of the cables 436, 438 is reduced, the plate 414 and cables 436, 438 cooperate to apply a clamping force to the portion of an arm 416. When sufficient clamping force is applied, plate 414 and cables 436, 438 cooperate to rigidly hold the portion of an arm 416 within the arm sheath 412. A release lever (not shown) is used to release tension in the cables 436, 438 and allow the arm sheath 412 to be removed from the portion of an arm 416.

The arm sheath 412 also includes a load system 490 configured to place the arm 416 in tension. The arm sheath 412 includes a weight 492 coupled to an end 494 of the plate 414 via a cable 496. A pulley 498 is positioned between the weight 492 and the plate 414 to guide the cable 496.

Although certain illustrative embodiments have been described in detail above, variations and modifications exist within the scope and spirit of this disclosure as described and as defined in the following claims.

The invention claimed is:

1. A surgical support apparatus comprising
a surgical boot sized to receive a portion of a limb of a patient therein, the surgical boot including a shell configured to receive a heel of the patient and a tongue positioned opposite the heel, and
a tightening device positioned between a first end and a second end of the surgical boot, the tightening device including a rotary tightening mechanism attached to the tongue and a cable extending from a first end attached to the rotary tightening mechanism, through a first guide defined in the tongue, through a second guide defined in the shell, and to a second end attached to the rotary tightening mechanism,
wherein the tightening device is configured to draw the tongue toward the shell such that a clamping force is configured to be applied to the portion of the limb of the patient positionable in the surgical boot.

2. The surgical support apparatus of claim 1, wherein the rotary tightening mechanism includes
a reel body coupled to the tongue, the reel body receives the first and second ends of the cable, and
a knob rotatively coupled to the reel body such that rotating the knob in a first direction draws each end of the cable into the reel body and draws the tongue toward the shell.

3. The surgical support apparatus of claim 1, further comprising
a cradle coupled to the shell, and
a handle removably coupled to the cradle, the handle having a channel defined therein, wherein the cable extends through the channel between the rotary tightening mechanism and the first guide.

4. The surgical support apparatus of claim 3, wherein the second guide is positioned on a first side of the shell and the cradle is attached to a second side of the shell opposite the first side.

5. The surgical support apparatus of claim 4, wherein the cable extends through the first guide in a first direction, through the second guide in a second direction, and through the channel in a third direction, the second direction is transverse to the first direction, and the third direction is generally parallel with the second direction when the handle is coupled to the cradle.

6. The surgical support apparatus of claim 3, wherein the tongue is attachable to the shell by the cable such that the tongue is attached to the shell when the handle is coupled to the cradle and detached from the shell when the handle is uncoupled from the cradle.

7. The surgical support apparatus of claim 1, further comprising a second tightening device positioned between the tightening device and the first end of the surgical boot.

8. The surgical support apparatus of claim 7, wherein the second tightening device is a strap mechanism.

9. The surgical support apparatus of claim 8, wherein the strap mechanism includes
a ladder strap extending over the tongue of the surgical boot, and
a buckle coupled to the shell of the surgical boot, the buckle being sized to receive the ladder strap.

10. The surgical support apparatus of claim 9, wherein
the ladder strap has a plurality of teeth, and
the buckle includes a clasp configured to engage with the plurality of teeth to draw the tongue toward the shell.

11. A surgical support apparatus comprising
a surgical boot sized to receive a portion of a limb of a patient therein, the surgical boot including a shell configured to receive a heel of the patient and a tongue positioned opposite the heel, a rotary lacing system positioned between a first end and a second end of the surgical boot, the rotary lacing system including a rotary tightening mechanism coupled to the tongue, a cable extending from a first end attached to the rotary tightening mechanism to a second end attached to the rotary tightening mechanism, a cradle coupled to the shell, and a handle removably coupled to the cradle, the handle having a channel defined therein a strap mechanism positioned between the rotary lacing system and the first end of the surgical boot, wherein the rotary lacing system and the strap mechanism are configured to draw the tongue toward the shell such that a clamping force is configured to be applied to the portion of the limb of the patient positionable in the surgical boot, wherein the cable extends through the channel of the handle between the first and the second ends of the cable.

* * * * *